United States Patent [19]

Terashima

[11] Patent Number: 5,308,767
[45] Date of Patent: May 3, 1994

[54] METHOD FOR CONTROL OR CALIBRATION IN A CHEMICAL ANALYTICAL DETERMINATION

[75] Inventor: Masaaki Terashima, Saitama, Japan

[73] Assignee: Fuji Photo Film Co., Ltd., Kanagawa, Japan

[21] Appl. No.: 915,290

[22] Filed: Jul. 20, 1992

Related U.S. Application Data

[63] Continuation-in-part of Ser. No. 318,229, Mar. 2, 1989, abandoned, which is a continuation-in-part of Ser. No. 115,726, Nov. 2, 1987, abandoned.

[30] Foreign Application Priority Data

Oct. 31, 1986 [JP] Japan ................. 61-259797
Nov. 18, 1986 [JP] Japan ................. 61-274919

[51] Int. Cl.⁵ ..................... G01N 31/00; G01N 21/77
[52] U.S. Cl. .................................. 436/12; 436/8; 436/14; 436/16; 436/170; 422/57; 422/69
[58] Field of Search ............ 436/8, 10, 12, 13, 14, 436/15, 16, 164, 169, 170; 422/68.1, 69, 56, 57

[56] References Cited

U.S. PATENT DOCUMENTS

| | | | |
|---|---|---|---|
| H600 | 3/1989 | Tanaka et al. | 422/56 |
| H602 | 3/1989 | Terashima | 436/18 |
| H623 | 4/1989 | Miyazako | 456/170 |
| 3,380,929 | 4/1968 | Petersen | 436/11 |
| 3,466,249 | 9/1969 | Anderson | 436/10 |
| 3,681,255 | 8/1972 | Wilfore | 436/11 |
| 3,778,381 | 12/1973 | Rosano et al. | 436/11 |
| 3,823,091 | 7/1974 | Samejima et al. | 436/11 |
| 3,859,049 | 1/1975 | Ware et al. | 436/11 |
| 3,977,995 | 8/1976 | Louderback et al. | 436/10 |
| 3,993,581 | 11/1976 | Yokoyama et al. | 252/312 |
| 4,163,734 | 8/1979 | Sorensen et al. | 436/11 |
| 4,781,890 | 11/1988 | Arai et al. | 422/56 |
| 4,786,595 | 11/1988 | Arai et al. | 435/25 |
| 4,877,579 | 10/1989 | Yazawa et al. | 422/56 |
| 4,902,477 | 2/1990 | Katsuyama et al. | 422/56 |
| 4,990,457 | 2/1991 | Tanaka et al. | 436/170 |
| 5,122,451 | 6/1992 | Tanaka et al. | 435/74 |
| 5,130,258 | 7/1992 | Makino et al. | 436/169 |

FOREIGN PATENT DOCUMENTS 2139703 1/1973 France.

Primary Examiner—James C. Housel
Assistant Examiner—N. Bhat
Attorney, Agent, or Firm—Sughrue, Mion, Zinn, Macpeak & Seas

[57] ABSTRACT

A method for control or calibration in a chemical analytical determination using a dry analysis element comprising at least one color-producing reagent and a porous layer, wherein the method comprises applying an aqueous dispersion onto the porous layer and measuring the optical density of the color produced, wherein the aqueous dispersion comprises a substance which is the same as or similar to an analyte to be determined and water-insoluble particles dispersed therein, wherein the particles are particles of a homopolymer, a copolymer, phthalates, trimellitates, phosphates, benzoates, amides, phenols, aliphatic esters, hydrocarbons, halogenated hydrocarbons, adipates, sebacates and natural polymers.

17 Claims, 2 Drawing Sheets

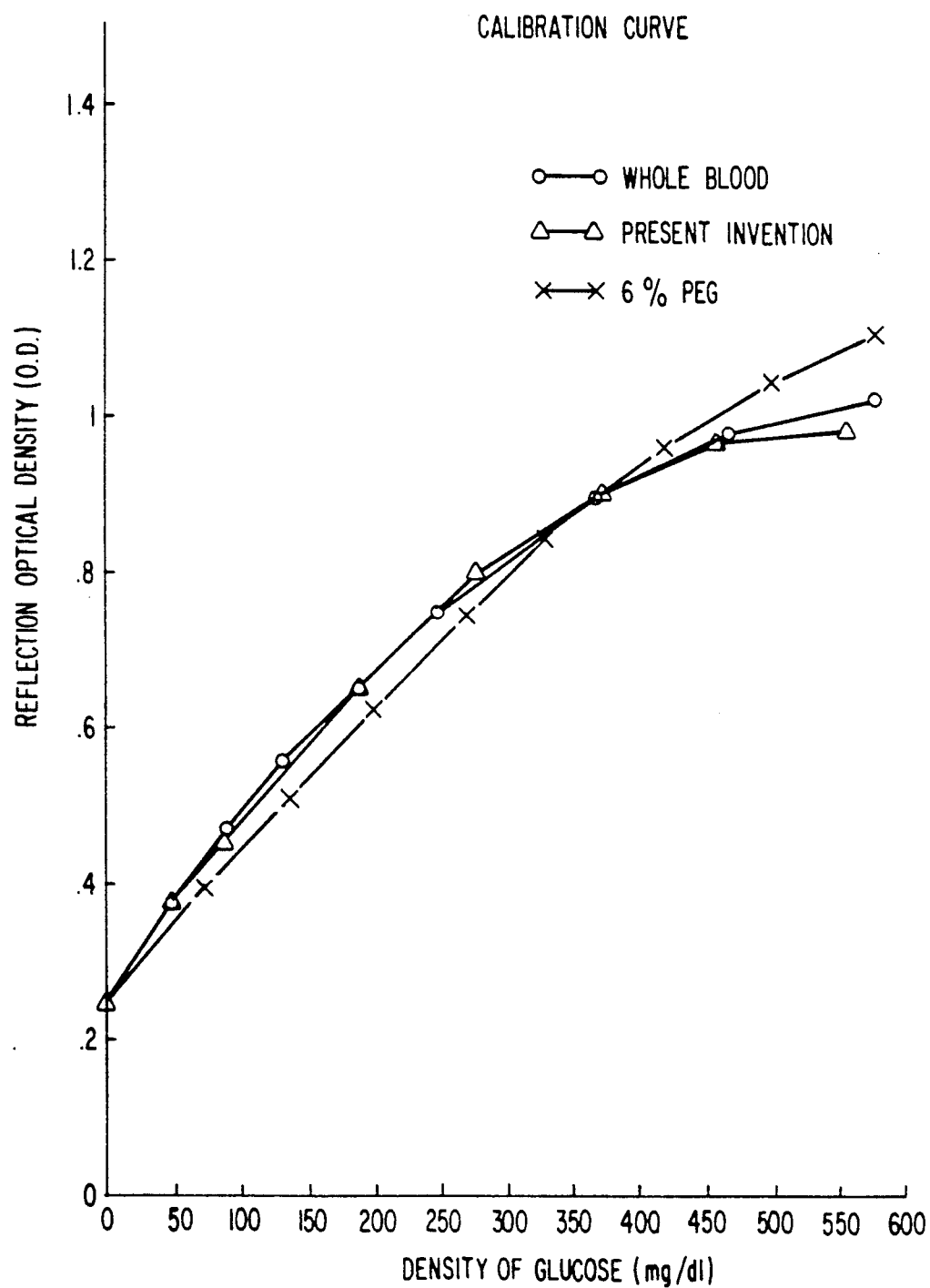

METHOD FOR CONTROL OR CALIBRATION IN A CHEMICAL ANALYTICAL DETERMINATION

CROSS REFERENCES TO RELATED APPLICATION

This application is a continuation-in-part of U.S. Ser. No. 07/318,229, filed Mar. 2, 1989 now abandoned which is a continuation-in-part of U.S. Ser. No. 07/115,726, filed Nov. 2, 1987 (now abandoned).

FIELD OF THE INVENTION

The present invention relates to a method for chemical analytical determination using a dry analytical element and a novel aqueous dispersion for control of the precision of the analytical element or for making a calibration curve in quantitatively analyzing a target component (an analyte) in samples of organic body fluids, such as whole blood, using dry analysis materials. More specifically, it is concerned with a method which is particularly useful in quantitatively analyzing whole-blood samples with dry analysis elements.

BACKGROUND OF THE INVENTION

Dry analysis materials and methods for quantitative analysis of aqueous fluid sample utilizing them are described in U.S. Pat. Nos. 2,846,808, 3,016,292, 3,036,893, 3,368,872 and 3,552,928.

Dry, multilayer analysis materials composed of a transparent support having thereon at least one reagent layer and a porous layer, in this order, and quantitative analysis methods of aqueous fluid samples using those materials are described, e.g., in U.S. Pat. Nos. 3,992,158, 3,983,005, 4,042,335, 4,066,403, 4,144,306, 4,132,528, 4,258,001, 4,357,363, 4,381,921 and 4,292,272 and Japanese Unexamined Patent Publication No. 24576/81, H.G. Curme et al. and R.W. Spayd et al., *Clinical Chemistry*, vol. 24, pp. 1,335–1,350 (1978), Bert Walter, *Anal. Chem.*, vol. 55, No. 4, pp. 498≈514 (1983) and so on. The feasibility of using not only diluted serum and blood plasma as a sample, but also non-diluted whole blood, is described.

More specifically, examples of clinical tests to determine blood-glucose concentrations within a short time by using non-diluted whole blood as a sample and a multilayer-film analytical element are described in Ohkubo et al, Clinical Chemistry, vol 27, pp. 1,287–1,290 (1981).

Such materials typically contain a porous spreading layer that filters out at least a good portion of the solid components of whole blood, allowing the fluid component to pass through to a color-forming reagent layer or layers.

It is required that the porous spreading layer permit a drop of aqueous fluid sample applied thereto first to spread rapidly in a circle in the horizontal direction and then, to penetrate in a vertical direction, supplying the aqueous fluid to the reagent layer located thereunder in an approximately constant volume per unit area. This function is called a spreading function or a metering function. Cotton or polyester fabrics and knits, membrane filter-form nonfibrous isotropic porous materials, porous materials made of bound granules, paper such as filter paper for chemical analysis, e.g., Toyo Roshi No. 2 made by Toyo Roshi Co., Ltd., and so on satisfy these requirements. In particular, employing textile fabrics, knits, or granular constructions of fine granules containing continuous pores described in U.S. Pat. Nos. 4,258,001, 4,357,363 and 4,381,921 permits the quantitative analysis of whole blood, because the materials possess a spreading function with respect to not only blood plasma and serum but also whole blood containing a solid component.

When the quantitative analysis of a particular analyte in sample solutions, especially whole blood, blood plasma, serum, urine and similar samples, is performed in clinics, periodic measurements are generally performed using a solution containing the analyte in a definite amount in order to determine the precision of the analysis system. The solution used is, in general, called a control solution or a standard solution. In addition, solutions containing the analyte in known amounts are used for preparing a calibration curve. These solutions are generally called calibrators of calibration solutions by those skilled in the art.

Although pooled blood obtained by mixing a number of whole-blood specimens, or pooled sera prepared by mixing serum samples are adopted as a control solution and calibration solutions in some cases, the composition varies with the lot. Further, pooled blood and serum are difficult to preserve. Therefore, calibration solutions are generally simple aqueous solutions containing given amounts of analyte alone, or additionally containing a hydrophilic polymer (e.g., polyvinyl alcohol, polyvinyl pyrrolidone, polyethylene glycol, etc.), plasma protein, or the like. (The aqueous solutions containing plasma protein are, in general, prepared by re-dissolving the lyophilized solid matter in water at the time of use.)

When calibration solutions of this kind are applied to the quantitative analysis of a particular component in fluid with dry analysis elements, particularly whole-blood analyses with dry analysis elements, the required color-producing reaction does not take place uniformly in the reagent layer(s). Accordingly, the application of such calibration solutions has the disadvantage that within-run reproducibility (precision) in color density measurements is poor. Moreover, since there is a difference in response to the analyte content, e.g., in color formation, between such calibration solutions and whole-blood samples, a calibration curve based on such calibration solutions has the defect that it deviates from the true calibration curve of whole-blood samples.

SUMMARY OF THE INVENTION

An object of the present invention is to improve the precision of the chemical analysis for determining an analyte in whole blood by the use of a dry analysis element, said analyte being solid or liquid at ordinary temperature, i.e., between 15° C. to 40° C.

More specifically, an object of the present invention is to provide a novel aqueous dispersion used for control or calibration in chemical analysis of whole-blood samples using dry analysis elements, which, in calibration, have the same response to an analyte content as whole-blood samples, thus providing a calibration curve that matches the true calibration curve of whole-blood samples, and in precision checking of the analysis system, providing excellent reproducibility.

A second object of the present invention is to provide an analysis method which can ensure high accuracy of data by using the above-described aqueous dispersion.

In order to achieve the aforementioned and other objects and advantages, the present invention is directed to a method for control or calibration in a chemical analytical determination using a dry analysis element, said dry analysis element comprising at least one color-producing reagent and a porous layer, comprising the steps of:

applying an aqueous dispersion onto the porous layer of the dry analysis element; and measuring optical density of the color produced, wherein the aqueous dispersion comprises a substance which is the same as or similar (with respect to color forming ability) to an analyte to be determined and water-insoluble particles dispersed therein and is directed to an aqueous dispersion used therein.

BRIEF DESCRIPTION OF THE DRAWINGS

The control or calibration liquids used in the present invention are now described in greater detail.

A particular substance contained in the control or calibration liquid is the same as or similar to the particular analyte to be analyzed and is dissolved or dispersed in the water phase. The amount of the particular substance preferably contained in the water phase is selected from the same amount range as that of the analyte in the specimen. Preferably particular substances contained in the control or calibration liquid and preferable amounts thereof are shown in the following Table 1. The amounts shown in the Table 1 are based on the amount of the control or calibration liquid.

TABLE 1

| Analyte | Particular Substance | *Preferable Addition Amount of Particular Substance | *More Preferable Addition Amount of Particular Substance | Particle diameter |
| --- | --- | --- | --- | --- |
| Glucose | Glucose | 0 to 2000 mg/dl | 20 to 1000 mg/dl | |
| Urea | Urea | 0 to 1000 mg/dl** | 5 to 200 mg/dl** | |
| Uric Acid | Uric Acid | 0 to 100 mg/dl | 2 to 50 mg/dl | |
| Creatinine | Creatinine | 0 to 100 mg/dl | 0.5 to 50 mg/dl | |
| Bilirubin | Bilirubin | 0 to 100 mg/dl | 0.2 to 50 mg/dl | |
| Hemoglobin | Hemoglobin, Red dyes | 0 to 100 g/dl | 5 to 50 g/dl | |
| Triglyceride | Trioleine | 0 to 2000 mg/dl | 50 to 1000 mg/dl | 0.2 μm or less |
| Triglyceride | Glycerine**** | 0 to 220 mg/dl | 5 to 1000 mg/dl | |
| Total cholesterol | Cholesterol | 0 to 2000 mg/dl | 50 to 1000 mg/dl | 0.2 μm or less |
| $NH_4^+$ | $(NH_4)_2SO_4$, $NH_4Cl$ | 0 to 3000 μg/dl** | 20 to 2000 μg/dl** | |
| $Ca^{2+}$ | $CaCl_2$, $Ca(NO_3)_2$ | 0 to 100 mg/dl*** | 5 to 20 mg/dl*** | |
| $Mg^{2+}$ | $MgCl_2$ | 0 to 100 mg/dl | 1 to 10 mg/dl | |
| $HPO_4^{2-}$ | $K_2HPO_4$ | 0 to 100 mmol | 0.5 to 5 mmol | |
| $SO_4^{2-}$ | $(NH_4)_2SO_4$ | 0 to 100 mmol | 0.1 to 5 mmol | |
| $NO_3^-$ | $Ca(NO_3)_2$, $NaNO_3$ | 0 to 100 mmol | 0.1 to 5 mmol | |

Figure 1:
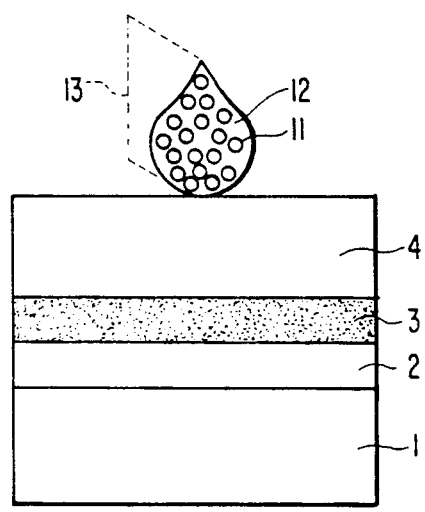
Figure 2:
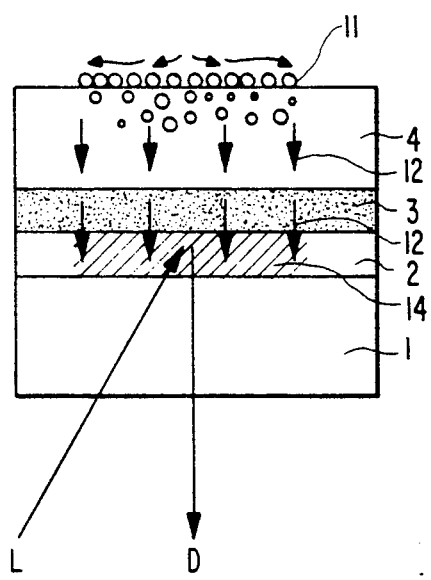

*Based on the control or calibration solution
**Calculated on the basis of nitrogen
***Calculated on the basis of calcium
****Glycerin is a hydrolysis product of trioleine FIG. 1 and FIG. 2 are diagrams illustrating schematically a whole-blood analysis in which a multi-layer-film analytical material is employed as a dry analytical element.

FIG. 3 depicts curves obtained from various kinds of calibration solutions.

DETAILED DESCRIPTION OF THE INVENTION

The aqueous dispersion used in the present invention contains a definite amount of particular substance which is the same as or similar to the substance to be analyzed and a water-insoluble dispersed particles. This aqueous dispersion can be used to check the normality of an analysis system and/or make a calibration curve.

The analysis method of the present invention is used for determining a particular analyte in whole-blood samples, in which a dry analysis element, such as an element comprising paper, containing at least one color-producing reagent in a water-permeable layer and having a porous spreading layer as the topmost layer is employed as an analyzing means.

A calibration curve is determined in advance using the aqueous dispersion containing water-insoluble dispersed particles. The amount of the particular analyte in whole blood to be tested is determined on the basis of the calibration curve.

The aqueous dispersion functioning either as control or calibration liquid is referred to as a control or calibration liquid hereinafter.

Other substances used in the present invention also include lipid, neutral fat, various enzymes such as amylase, lactate dehydrogenase, etc. and so on.

A dispersion which contains no particular substance may be used in the present invention as a calibrating liquid for blank (zero level) calibration.

When the water-insoluble dispersed phase is a solid phase comprising solid particles, examples of the material used for preparing the solid particles include styrene homopolymers; copolymers prepared from styrene and comonomers copolymerizable with styrene; acrylate homopolymers, copolymers prepared from acrylates and comonomers copolymerizable with acrylates; vinyl acetate homopolymer, copolymers prepared from vinyl acetate and comonomers copolymerizable with vinyl acetate; vinyl chloride homopolymers and copolymers prepared from vinyl chloride and comonomers copolymerizable with vinyl chloride. Above-described copolymerizing comonomers can be chosen from any conventionally used monomers provided that the resulting copolymers are insoluble in water.

The homopolymers and copolymers described above preferably have a molecular weight of from $10^5$ to $10^6$.

Preferable comonomers copolymerizable with the above described monomer include butadiene, vinyl chloride, acrylamide, acrylic acid and methacrylic acid. The comonomer ratio in the copolymer is preferably from 0 to 90 mol % based on the total amount of monomers in the copolymer.

Preferred examples of solid particles in the solid phase includes a styrene-acrylic acid copolymer having a monomer ratio of styrene to acrylic acid of from 50 to 100 mol % and having a molecular weight of $10^5$ to $10^6$.

When the water-insoluble dispersed phase is a liquid phase comprising liquid particles, examples of the liquid include adipates, sebacates, phthalates, trimellitates and phosphates, as disclosed in, Japanese Patent Application (OPI) No. 122956/81, wherein the alcohol moiety thereof is preferably derived from an alcohol selected from methanol, ethanol, isopropanol, butanol, octanol, decanol, cyclohexanol, phenol, cresol etc.

Preferred examples of liquid particles in the liquid phase include phthalic acid diesters such as dibutylphthalate, cyclohexylphthalate, di-2-ethylhexylphthalate, decylphthalate, etc.; phosphates such as triphenylphosphate, tricresylphosphate, 2-ethylhexyldiphenylphosphate, tricyclohexylphosphate, tri-2-ethylhexylphosphate, etc., benzoates such as 2-ethylhexylbenzoate, etc.; amides such as N,N-diethyllaurylamide, N-tetradecylpyrrolidone, etc.; phenols such as 2,4-di-t-amylphenol, etc.; aliphatic esters such as trioctylcitrate, etc., hydrocarbons such as paraffin, etc.; halogenated hydrocarbons such as chloroparaffin, etc.

Further, the water-insoluble dispersed phase may be comprised of natural polymers such as sodium alginate, etc.

The control or calibration liquid used in the present invention may be in the form of an emulsion or a suspension of particles having a mean size which ranges from about 0.01 $\mu$m to about 10 $\mu$m, preferably from about 0.05 82 m to about 6 $\mu$m and most preferably from about 0.2 $\mu$m to about 2 $\mu$m. If the phase to be dispersed can be mixed homogeneously with a water phase by a simple stirring operation, the phase may be employed in the present invention, that is, it may be used as long as the phase can be dispersed in water as a homogeneous dispersion by simple agitation such as gentle shaking. The size of the particles can be controlled and measured using conventional methods.

The solubility of the water-insoluble particles is preferably less than 0.1 wt % in water.

The water-insoluble particles are contained in an amount of from 1 to 50 wt %, preferably from 10 to 50 wt % based on the total weight of the dispersion.

Other additives which may be contained in the control or calibration liquid include surface active substances, defoaming agents, antiseptics, etc., if desired, provided that they do not adversely affect the intended analyses. Organic solvents, for example, alcohols, such as methanol, ethanol, benzyl alcohol; and other organic liquid substances can be also added to the control or calibration liquid of the present invention.

Suitable examples of dispersants include a polyethyleneglycol, an alkylphenoxypolyethoxyethanol, e.g., p-nonylphenoxypolyethoxyethanol (containing ethoxy units of 10 to 40).

Suitable examples of the antiseptics include parachlorophenol derivatives and benzothiazole derivatives described in Japanese Unexamined Patent Publication Nos. 214342/87 and 245955/87.

The present invention is useful for analysis of particular analytes in fluids by the use of multilayer-film, dry analytical elements described, e.g., in Japanese Patent Publication No. 53888/74, Japanese Unexamined Patent Publication Nos. 137192/75, 140191/76, 3488/77, 131089/78, 101398/79, 90859/80, 164356/80 and 24576/81. In particular, the invention is useful for analysis of whole blood. Also it can be utilized in analyzing blood plasma, serum, urine, saliva, etc. Further, it is useful for analyses performed using whole-blood analysis elements. These elements are described in Japanese Unexamined Patent Publication Nos. 4959/86, 138756/87, 138757/87 and 138758/87.

Examples of analyte preferably include glucose, urine, uric acid, creatinine, hemoglobin, bilirubin, triglyceride, glycerine, cholesterol, $NH_4^+$, $Ca^{2+}$, $Mg^{2+}$, $Cl^-$, $HPO_4^{2-}$, $SO_4^{2-}$, $NO_3^-$, etc.

A method of analyzing whole-blood samples using a dry analysis element is illustrated schematically in FIG. 1 and FIG. 2.

The exemplified multilayer-film analytical element is a film analyzer having a multilayer structure provided with a reagent layer 2, light-reflecting layer 3 and a porous spreading layer 4 on one side of a transparent support 1 (of course, plural reagent layers, a barrier layer, a scavenger layer, a buffer layer, a detector layer and so on may be interposed between the support and the spreading layer, if needed).

When a blood sample 13 comprising a solid component 11 and a fluid component 12 is spotted on the porous spreading layer 4 of a multilayer analysis film, the whole blood spreads in a circle over the spreading layer, and area of the circle is approximately proportional to the quantity spotted thereon. Then, the fluid component alone passes through the porous spreading layer as the solid component is filtered out, and successively passes through the light-reflecting layer 3, and finally arrives at the reagent layer 2.

In principle, a selective color-producing reagent capable of reacting only with a particular analyte in the blood is incorporated in the reagent layer in advance, so color development takes place in proportion to the content of the analyte. The optical density of the color in the color-developed region 14 is measured with a colorimeter from the support side by comparing illuminating light and reflected light. Thereby the content of the analyte in the blood can be determined by colorimetry.

FIG. 1 illustrates the application of a drop of whole blood 13 to the porous spreading layer 4. FIG. 2 illustrates the movement of whole blood after spotting. Specifically, the solid component 11 (blood cells, etc.) is filtered off by the porous spreading layer 4 to remain in the vicinity of the surface of the spreading layer, while the fluid component 12 passes through the light-reflecting layer 3, and reaches the reagent layer 2.

In these figures, 1 designates a transparent support, 14 a color-developed region, L the direction of illumination light from a light source, and D the direction of reflected light.

Calibration curves determined from various calibration solutions are shown in FIG. 3.

The present invention is illustrated in greater detail by reference to the following examples, but the present invention is not to be construed as being limited thereto.

EXAMPLE 1

In order to determine glucose concentrations in whole-blood samples, dry chemical analysis slides and control liquid were prepared in the following manner.

A coating composition for forming a reagent layer, which contained the following amounts of ingredients, was coated in a dry thickness of 15 $\mu$m on a 180 $\mu$m-thick smooth film of polyethylene terephthalate film having a gelatin substratum, and dried.

| | |
|---|---|
| Gelatin | 20 g |
| Peroxidase | 2,500 IU |
| Glucose oxidase | 1,000 IU |
| 1,7-Dihydroxynaphthalene | 0.5 g |
| 4-Aminoantipyrine | 0.5 g |
| Nonylphenoxypolyethoxyethanol (oxyethylene units: about 40) | 0.2 g |
| Water | 200 ml |

On the reagent layer, a coating composition for forming a light shielding layer, which contained the following amounts of ingredients, was coated in a dry thickness of 7 μm, and dried.

| | |
|---|---|
| Gelatin | 10 g |
| Titanium dioxide (average particle diameter: 0.3 μm) | 100 g |
| Water | 500 ml |

On the light shielding layer, an adhesive composition containing the following amounts of ingredients was coated in a dry thickness of 2 μm, and dried.

| | |
|---|---|
| Gelatin | 4 g |
| Nonylphenoxypolyethoxyethanol (oxyethylene units: about 40) | 0.1 g |
| Water | 200 ml |

After the adhesive was moistened with 30 g/m² of water, cotton broad cloth (80 yarn counts) was adhered by applying light pressure thereto, and dried.

The thus prepared glucose analysis film was cut into pieces measuring 15 mm by 15 mm in size, and each piece was put on a plastic mount measuring 24 mm by 28 mm in size.

Liquids I and II according to the invention having the following compositions respectively were prepared as a control solution.

| | |
|---|---|
| Composition of Liquid I: | |
| Voncoat PP-1001* | 500 g |
| Distilled water | 500 g |
| Glucose | 0.650 g |
| Suraofu 72N** | 0.2 g |
| Composition of Liquid II: | |
| Voncoat PP-1001* | 500 g |
| Distilled water | 500 g |
| Glucose | 2.100 g |
| Suraofu 72N** | 0.2 g |

*a dispersion of acryl-styrene resin particles; (mean particle size: 0.2 to 0.6 μm; solid content (polymer): 50 wt %; produced by Dai-Nippon Ink & Chemicals, Inc.
**antiseptics produced by Takeda Chemical Industries, Ltd.

Of the 40 slides for dry analysis of glucose, 20 slides were used for spotting of the foregoing liquid I, and the remaining 20 slides were used for spotting of the foregoing liquid II. Densities of the developed color were measured with a Fuji DriChem DC-1000 Glucose Analyzer (produced by Fuji Photo Film Co., Ltd.), and within-run reproducibility was examined.

For the purpose of comparison, two control liquids prepared by adding different amounts of glucose to a 7% polyethylene glycol (PEG) solution (molecular weight 20,000), and two fresh whole-blood specimens obtained by adding different amounts of glucose to fresh blood taken with a heparin-coated tube syringe were subjected to the same measurement as described above. Each fluid was spotted on 20 slides in the same manner as above, and reproducibilities thereof were compared with those of the present control liquids.

The results obtained are shown in the following Table 2.

As can be seen from the data in the Table 2, the control liquids of the present invention were excellent in reproducibility (coefficient of variation, abbreviated as CV), compared with the control liquids, and were equivalent to fresh whole blood in reproducibility.

TABLE 2

| Whole blood | | Invention | | Comparison 7% PEG | |
|---|---|---|---|---|---|
| Glucose Concentration (mg/dl) | | | | | |
| 102 | 327 | 112 | 264 | 88 | 292 |
| 102 | 318 | 114 | 261 | 86 | 292 |
| 106 | 319 | 113 | 277 | 89 | 294 |
| 102 | 314 | 113 | 271 | 90 | 295 |
| 105 | 325 | 115 | 269 | 89 | 294 |
| 105 | 316 | 113 | 273 | 90 | 288 |
| 104 | 316 | 114 | 272 | 87 | 288 |
| 105 | 319 | 115 | 264 | 89 | 283 |
| 107 | 320 | 114 | 267 | 89 | 283 |
| 105 | 316 | 111 | 264 | 90 | 279 |
| 104 | 312 | 111 | 270 | 88 | 289 |
| 107 | 318 | 113 | 272 | 93 | 292 |
| 106 | 314 | 112 | 266 | 91 | 297 |
| 102 | 313 | 113 | 266 | 90 | 292 |
| 105 | 312 | 113 | 270 | 86 | 292 |
| 105 | 314 | 115 | 264 | 87 | 283 |
| 102 | 319 | 116 | 261 | 86 | 262 |
| 104 | 316 | 115 | 273 | 86 | 288 |
| 104 | 327 | 117 | 272 | 89 | 292 |
| 105 | 348 | 114 | 269 | 88 | 289 |
| x̄ | 104 | 318 | 114 | 268 | 89 | 288 |
| SD | 1.63 | 4.57 | 1.53 | 4.23 | 1.88 | 7.75 |
| CV | 1.56 | 1.44 | 1.34 | 1.58 | 2.12 | 2.69 | x̄: average value
SD: standard deviation
CV: coeffecient of variation

As is apparent from the results, comparative solution containing 7% of polyethylene glycol, which does not compose a dispersed phase provides a large C.V. value of over 2%. On the other hand, the calibration liquid of the present invention provides a C.V. value of 2% or less, which value is almost the same as that of whole blood, and, thus, reproducibility is excellent.

EXAMPLE 2

For the purpose of determination of glucose concentrations, dry chemical analysis slides and calibration liquids were prepared in the same manner as in Example 1.

Liquids III, IV and V having the following compositions respectively were prepared as primary glucose calibration liquids.

| | |
|---|---|
| Composition of Liquid III: | |
| Distilled water | 360 g |
| Glucose | 0.500 g |
| Cebian A46774* | 640 g |
| Suraofu 72N* | 0.2 g |
| Composition of Liquid IV: | |
| Distilled water | 360 g |
| Glucose | 2.000 g |
| Distilled water | 360 g |
| Composition of Liquid III: | |
| Cebian A46774* | 640 g |
| Suraofu 72N** | 0.2 g |
| Composition of Liquid V: | |
| Distilled water | 360 g |
| Glucose | 5.000 g |
| Cebian A46774* | 640 g |

| | |
|---|---|
| -continued | |
| Suraofu 72N** | 0.2 g |

*styrene-ethyl acrylate copolymer (molar ratio 1:4; particle size: average 0.3 μm; polymer content 30 wt %) produced by Daicel Ltd.
**antiseptics produced by Takeda Chemical Industries Ltd.

The following three kinds of calibration liquids (a), (b) and (c) were prepared.

(a) Eight invention calibration liquids prepared by mixing the foregoing three primary liquids so that their respective glucose concentrations were within the range of from 0 to 600 mg/dl.

(b) Eight specimens of whole blood, which were prepared so as to have their respective glucose concentrations within the range of from 0 to 600 mg/dl.

(c) Eight comparison solutions, which were prepared by mixing three primary solutions containing 6 wt % of polyethylene glucol (molecular weight 20,000) and 0.500, 2.000 and 5.000 g/l of glucose, respectively.

Each of the eight calibration liquids (a) of the present invention were spotted on three separate glucoseanalysis slides described above. Also, the eight whole-blood specimens for calibration (b) and the eight comparison liquids (c) were spotted similarly. The densities of formed colors in these slides were measured with a Fuji DriChem DC-1000 Glucose Analyzer (made by Fuji Photo Film Co., Ltd.). The optical density of the colors developed in the three slides under the same conditions were averaged. The results obtained are shown in FIG. 3.

As can be seen from the graph of FIG. 3, the calibration curve obtained from the calibration liquids of the present invention was closer to that of whole blood than that obtained from the comparative calibration liquids.

What is claimed is:

1. A method for control or calibration in a chemical analytical determination using a dry analysis element, said dry analysis element comprising at least one color-producing reagent and a porous layer, comprising the steps of:

applying an aqueous dispersion onto the porous layer; and measuring optical density of the color produced, wherein the aqueous dispersion comprises a substance which is the same as or similar to an analyte to be determined and water-insoluble particles dispersed therein wherein said water-insoluble particles are solid particles or liquid particles, said solid particles being selected from the group consisting of homopolymers and copolymers and said liquid particles being selected from the group consisting of adipates, sebacates, phthalates, trimellitates, phosphates, benzoates, amides, phenols, aliphatic esters, hydrocarbons, halogenated hydrocarbons, and natural polymers.

2. The method as claimed in claim 1, wherein said water-insoluble dispersed particles are solid particles.

3. The method as claimed in claim 2, wherein said solid particles comprise a homopolymer or copolymer derived from a monomer selected from the group consisting of styrene, an acrylate, vinyl acetate and vinyl chloride.

4. The method as claimed in claim 3, wherein said copolymer is derived from said monomer and a comonomer selected from the group consisting of butadiene, vinyl chloride, acrylamide, acrylic acid and methacrylic acid.

5. The method as claimed in claim 4, wherein said homopolymers and copolymers have a molecular weight of from $10^5$ to $10^6$.

6. The method as claimed in claim 1, wherein said water-insoluble dispersed particles are liquid particles.

7. The method as claimed in claim 6, wherein said liquid particles comprise a compound selected from the group consisting of phthalates, trimellitates, phosphates, benzoates, amides, phenols, aliphatic esters, hydrocarbons and halogenated hydrocarbons.

8. The method as claimed in claim 1, wherein said water-insoluble dispersed particles have a mean particle size of from about 0.01 to about 10 μm.

9. The method as claimed in claim 1, wherein said water-insoluble dispersed particles are present in a concentration of about 10 to 50% by weight based on the total weight of the aqueous dispersion.

10. The method as claimed in claim 1, wherein said analyte to be determined comprises a component of whole blood.

11. The method as claimed in claim 1, wherein said analyte to be determined is selected from the group consisting of glucose, urea, uric acid, creatinine, bilirubin, hemoglobin, triglyceride, total cholesterol, $NH_4^+$, $Ca^{2+}$, $Mg^{2+}$, $HPO_4^{2-}$, $SO_4^{2-}$, and $NO_3^-$.

12. The method as claimed in claim 1, wherein said substance is selected from the group consisting of glucose, urea, uric acid, creatinine, bilirubin, hemoglobin, triolein, glycerine, cholesterol, $(NH_4)_2SO_4$, $NH_4Cl$, $CaCl_2$, $Ca(NO_3)_2$, $MgCl_2$, $NaCl$, $KCl$, $K_2HPO_4$, $(NH_4)_2SO_4$, $Ca(NO_3)_2$, and $NaNO_3$.

13. The method as claimed in claim 1, wherein said water-insoluble dispersed particles have a mean particle size of from 0.05 to 6 μm.

14. The method as claimed in claim 1, wherein said water-insoluble dispersed particles have a mean particle size of from 0.2 to 2 μm.

15. The method as claimed in claim 1, wherein the dry analysis element comprises paper containing at least one color-producing reagent.

16. The method as claimed in claim 1, wherein the dry analysis element comprises at least one color-producing reagent and a porous spreading layer.

17. The method as claimed in claim 1, wherein the dry analysis element comprises a transparent support having thereon on one side of the support at least one reagent layer comprising at least one color-producing reagent, a light reflecting layer and a porous spreading layer.

* * * * *